United States Patent [19]

Kelly

[11] 4,235,779
[45] Nov. 25, 1980

[54] BICYCLIC LACTONES

[75] Inventor: Robert C. Kelly, Kalamazoo, Mich.

[73] Assignee: The Upjohn Company, Kalamazoo, Mich.

[21] Appl. No.: 96,806

[22] Filed: Nov. 23, 1979

Related U.S. Application Data

[62] Division of Ser. No. 654,109, Feb. 2, 1976, abandoned.

[51] Int. Cl.³ .............................................. C07D 307/77
[52] U.S. Cl. .............................. 260/343.3 P; 542/426
[58] Field of Search .................. 260/343.3 P; 542/426

[56] References Cited

U.S. PATENT DOCUMENTS 3,904,648  9/1975  Kelly .............................. 260/343.3 P

FOREIGN PATENT DOCUMENTS 50-18460  2/1975  Japan ................................ 260/343.3 P Primary Examiner—Henry R. Jiles
Assistant Examiner—Jane T. Fan
Attorney, Agent, or Firm—Robert A. Armitage

[57] ABSTRACT

Process for preparing bicyclic lactone acrylic aldehydes and ketones of the formula

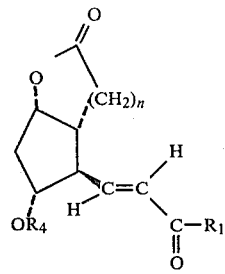

wherein "n" is one or 2, wherein $R_1$, is hydrogen, methyl, or ethyl, and wherein $R_4$ is hydrogen or a blocking group; and those aldehydes, ketones, and intermediates prepared therein. The aldehydes and ketones are useful intermediates in preparing prostaglandins and analogs having pharmacological utility.

2 Claims, No Drawings

BICYCLIC LACTONES

This is a division, of application Ser. No. 654,109, filed Feb. 2, 1976, now abandoned.

BACKGROUND OF THE INVENTION

This invention relates to intermediates useful in the preparation of prostaglandins and analogs, and to a process for preparing them.

The prostaglandins and analogs are well-known organic compounds derived from prostanoic acid which has the following structure and atom numbering:

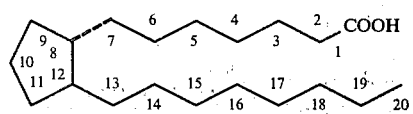

Among the prostaglandins are prostaglandin $F_{2\alpha}$, "$PGF_{2\alpha}$", and prostaglandin $F_{3\alpha}$, "$PGF_{3\alpha}$", which are represented by formulas II and III, respectively:

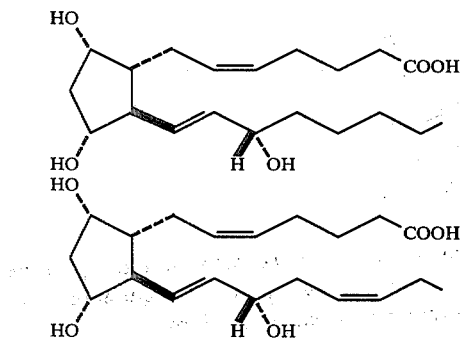

The prostaglandin formulas mentioned above each have several centers of asymmetry. As drawn, each formula represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins. For convenience hereinafter, use of the terms "$PGF_{2\alpha}$", "$PGF_{3\alpha}$", and the like, will mean the optically active form of that prostaglandin with the same absolute configuration as $PGE_1$ obtained from mammalian tissues.

In the formulas given above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Prostaglandins $F_{2\alpha}$ and $F_{3\alpha}$ are well known in the art, including methods of preparation and demonstrations of utility. See, for example, U.S. Pat. Nos. 3,706,789 and 3,804,879; Bergstrom et al., Pharmacol. Rev. 20, 1 (1968) and references cited therein; and E. J. Corey et al., J. Am. Chem. Soc. 92, 397 (1970) and 93, 1490 (1971).

One illustration of a prostaglandin analog is 16,16-dimethyl-$PGF_{2\alpha}$, represented by formula IV:

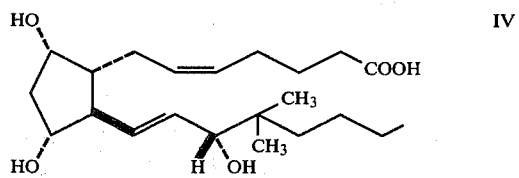

For background of this compound, see, for example, U.S. Pat. No. 3,903,131.

Also representative of prostaglandin analogs are 15-methyl- and 15-ethyl-$PGF_{2\alpha}$, represented by formula V:

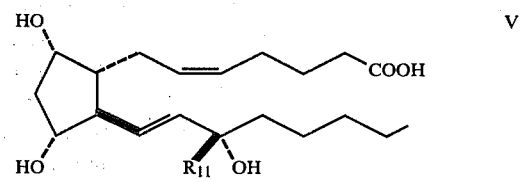

wherein $R_{11}$ is methyl or ethyl. For background on these compounds, see, for example, U.S. Pat. No. 3,728,382.

Still another illustration of a prostaglandin analog is 4,5-didehydro-$PGF_{1\alpha}$, represented by formula VI:

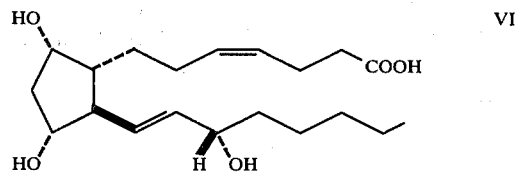

For background on this compound, see, for example, German Offenlegungsschrift No. 2,320,552.9, or the abstract in Derwent Farmdoc No. 69674U.

SUMMARY OF THE INVENTION

It is the purpose of this invention to provide novel intermediates useful in the preparation of prostaglandins and analogs commercially in substantial amount, with high purity, and at reasonable cost. It is a further purpose to provide processes for preparing these intermediates and for utilizing them.

Accordingly, there is provided a compound of the formula:

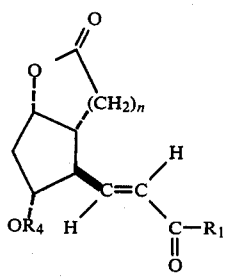 VII wherein n is one or 2; wherein $R_1$ is hydrogen, methyl, or ethyl; and wherein $R_4$ is (1) hydrogen, (2) tetrahydropyranyl, (3) tetrahydrofuranyl, (4) a group of the formula

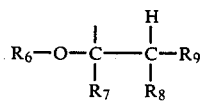

wherein $R_6$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_7$ and $R_8$ are the same or different, being hydrogen, alkyl of one to 4 carbon atoms, inclusive, phenyl or phenyl substituted with one, 2, or 3 alkyl of one to 4 carbon atoms, inclusive, or, when $R_7$ and $R_8$ are taken together, —$(CH_2)_a$— or —$(CH_2)_b$—O—$(CH_2)_c$— wherein a is 3, 4, or 5, b is one, 2, or 3, and c is one, 2, or 3 with the proviso that b plus c is 2, 3, or 4, and wherein $R_9$ is hydrogen or phenyl; (5) silyl of the formula —$Si(A)_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive; or (6) carboxyacyl including

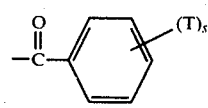 (a')

wherein T is alkyl of one to 4 carbon atoms, inclusive, phenylalkyl of 7 to 10 carbon atoms, inclusive, or nitro, and s is zero to 5, inclusive, provided that not more than to T's are other than alkyl, and that the total number of carbon atoms in the T's does not exceed 10 carbon atoms;

 (b')

wherein $R_{13}$ is alkyl of one to 4 carbon atoms, inclusive;

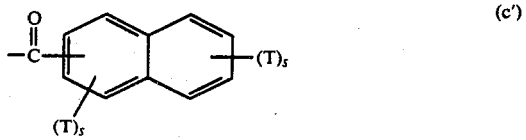 (c')

wherein T and s are as defined above; or

 (d')

wherein $R_{14}$ is alkyl of one to 7 carbon atoms, inclusive.

There is likewise provided a process for preparing compounds of formula VII above which comprises the steps of starting with a tricyclic aldehyde of the formula:

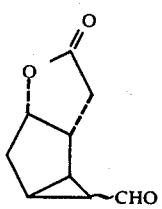 VIII wherein ~ indicates attachment of a group to the cyclopropane ring in exo or endo configuration, and (a) forming an alkene of the formula

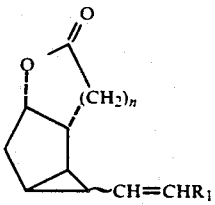 IX wherein n is either one or 2 and wherein $R_1$ and ~ are as defined above, by Wittig reaction with the ylid derived from a phosphonium bromide of the formula $R_1CH_2(C_6H_5)_3PBr$ wherein $R_1$ is as defined above;

(b) hydroxylating the product of step (a) to form a glycol of the formula

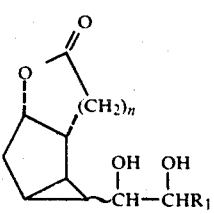 X wherein n, $R_1$ and ~ are as defined above;

(c) converting the glycol of step (b) to a compound of the formula

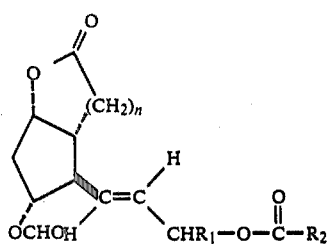

XI wherein n and $R_1$ are as defined above, and wherein $R_2$ is alkyl of one to 19 carbon atoms, inclusive, or aralkyl of 7 to 12 carbon atoms, inclusive, substituted with zero to 3 halo atoms, by stepwise reaction with (1) an ortho ester of the formula

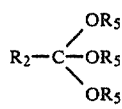

wherein $R_2$ is as defined above and $R_5$ is methyl or ethyl, and (2) anhydrous formic acid;

(d) removing the formyl groups from the product step (c) by solvolysis in the presence of a base;

(e) replacing the free hydroxyl groups of the product of step (d) to form a compound of the formula

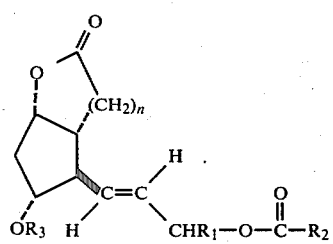

XII wherein n, $R_1$, and $R_2$ are as defined above, and wherein $R_3$ is a blocking group which is tetrahydropyranyl, tetrahydrofuranyl, or a group of the formula

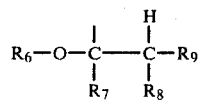

wherein $R_6$, $R_7$, $R_8$, and $R_9$ are as defined above.

There are likewise provided the novel intermediates of formulas IX–XV herein, useful in the synthesis of the formula-VII compounds.

Reference to Chart A, herein, will make clear the steps by which these compounds are obtained. The starting material of formula VIII, a tricyclic lactone aldehyde, is available from U.S. Pat. No. 3,816,462 in its various isomers, including the exo and endo forms as either of their optically active forms or as racemic mixtures. Either the exo or endo formula-VIII compound will yield the formula XI–XVI compounds of this invention shown in Chart A. For purposes herein, the endo form is preferred, in the optically active form which will yield $PGF_{2\alpha}$ in its natural configuration.

CHART A

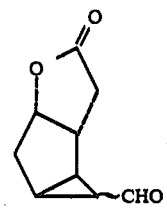

VIII (a)

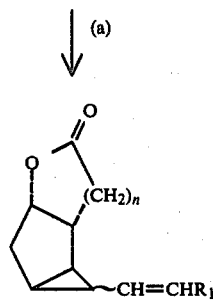

IX (b)

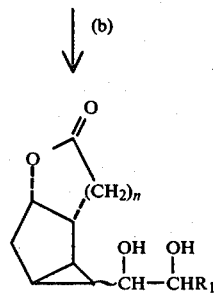

X (c)

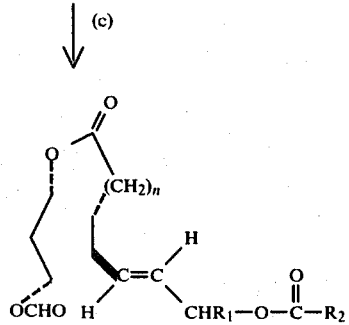

XI (d)

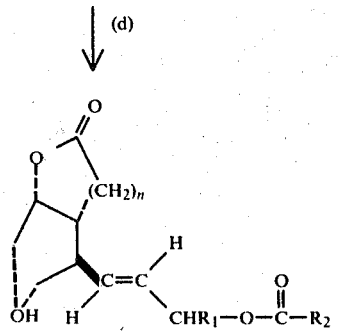

XV (e)

-continued
CHART A

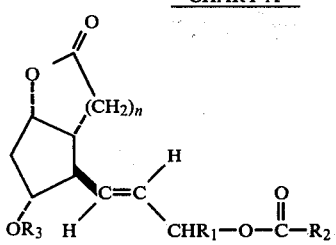
XII

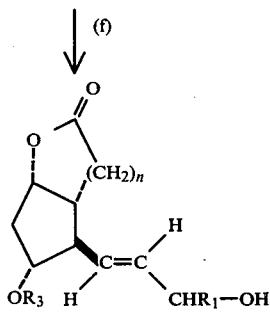
XIII

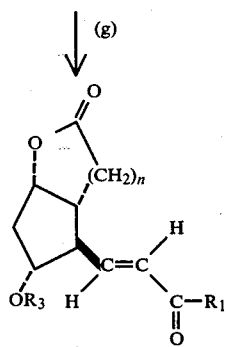
XIV

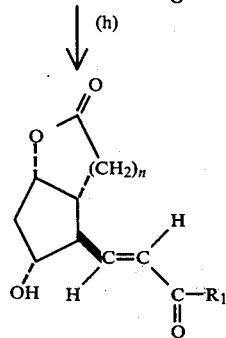
XVI

In Chart A, ~ indicates attachment of a group to the cyclopropane ring in endo or exo configuration; R₁ is hydrogen, methyl, or ethyl; R₂ is alkyl of one to 19 carbon atoms, inclusive, or aralkyl of 7 to 12 carbon atoms, inclusive, substituted with zero to 3 halo atoms; and R₃ is a blocking group which is tetrahydropyranyl, tetrahydrofuranyl, or a group of the formula

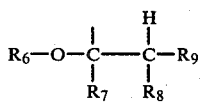

wherein $R_6$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_7$ and $R_8$ are the same or different, being hydrogen, alkyl of one to 4 carbon atoms, inclusive, phenyl or phenyl substituted with one, 2, or 3 alkyl of one to 4 carbon atoms, inclusive, or, when $R_7$ and $R_8$ are taken together, —(CH₂)a— or —(CH₂)b—O—(CH₂)c— wherein a is 3, 4, or 5, b is one, 2, or 3, and c is one, 2, or 3 with the proviso that b plus c is 2, 3, or 4, and wherein $R_9$ is hydrogen or phenyl. The latter group includes ethoxyethyl and methoxyisopropyl.

The blocking group, $R_3$, is a group which replaces hydrogen of the 3-hydroxyl groups, which is not attacked by nor is reactive to reagents used for oxidizing the side-chain hydroxyl of the formula-XIII compound to the aldeyde group in step (g), and which is easily removable under acidic conditions so as to be replaced by hydrogen. Blocking groups of various types, useful for various purposes, are known in the art. See, for example, J. F. W. McOmie, Protective Groups in Organic Chemistry, Plenum Press, N.Y., 1973.

Alkyl groups of one to 19 carbon atoms, inclusive, include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and isomeric forms thereof. Examples of aralkyl of 7 to 12 carbon atoms, inclusive, substituted with zero to 3 halo atoms, include benzyl, phenethyl, 1-phenylethyl, 2-phenylpropyl, 4-phenylbutyl, 3-phenylbutyl, 2-(1-naphthylethyl), 1-(2-naphthylmethyl), (2-chlorophenyl)methyl, and (2-bromo-2-phenyl)ethyl.

In step "a" of Chart A, tricyclic lactone aldehyde VIII is transformed to alkene IX by the Wittig reaction with the ylid derived from an alkyltriphenylphosphonium bromide. This general reaction is well known to those skilled in the art. See, for example, "The Wittig Reaction", Ylid Chemistry by A. William Johnson, Academic Press, N.Y., 1966. This reaction is run in various solvents, including benzene, toluene, tetrahydrofuran, or dimethyl sulfoxide, in a temperature range of from 0° to 100° C.

When "n" in formula IX is 2, those formula -IX intermediates are prepared from the product of step "a" described above by the following reactions. See Chart B, herein, and, for further elucidation, German Offenlegungsschrift No. 2,320,552 as abstracted in Derwent Farmdoc No. 69674U. In Chart B, $R_1$ is defined as in Chart A and $R_{12}$ is alkyl of one to 4 carbon atoms, inclusive. Examples of alkyl of one to 4 carbon atoms, inclusive, are methyl, ethyl, propyl, and butyl, and isomers thereof.

CHART B

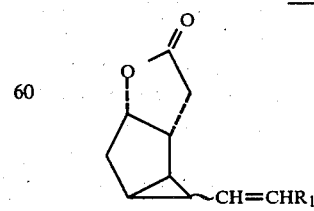
IX

(i)

-continued
CHART B

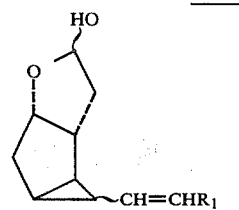   XVIII (j)

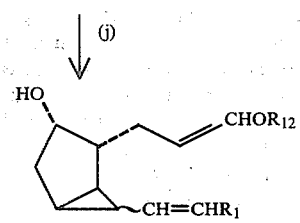   XIX (k)

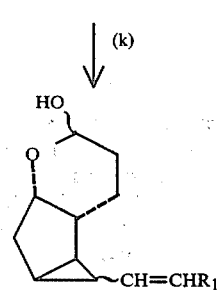   XX (l)

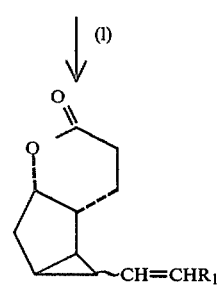   XXI

In step "i" of Chart B, the formula-IX lactone is reduced to the formula-XVIII lactol. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, the metal trialkoxy borohydrides, e.g., sodium trimethoxyborohydride. Especially preferred is diisobutylaluminum hydride at −60° to 70° C. The resulting alpha and beta hydroxy reduction products may be separated, for example by silica gel chromatography, but this step is usually not necessary since both are useful in the subsequent step (j).

In step "j" of Chart B, the formula-XVIII lactol undergoes condensation to form the formula-XIX enol ethers. For this purpose, an alkoxymethylenetriphenylphosphorane is useful. See, for example, Levine, J. Am. Chem. Soc. 80, 6150 (1958). The reagent is conveniently prepared from a corresponding quaternary phosphonium halide and a base, e.g. butyl lithium or phenyl lithium, at a low temperature, e.g. preferably below −10° C. The formula-XVIII lactol is mixed with the reagent and the condensation proceeds smoothly within the temperature range −30° C. to +30° C. At higher temperatures the reagent is unstable, whereas a low temperatures the range of condensation is undesirably slow. Examples of the alkoxy-methylenetriphenylphosphoranes preferred for forming the formula-XIX enol ethers are methoxy-, ethoxy-, propoxy-, isopropoxy-, butoxy-, isobutoxy-, sec-butoxy-, and tert-butoxymethylenetriphenylphosphorane. See Organic Reactions, Vol. 14, pages 346–348; John Wiley and Sons, Inc., N.Y. (1965).

Consider, next, step "k" of Chart B, wherein the formula-XIX enol ether intermediates are hydrolyzed and cyclized to the formula-XX lactols. This hydrolysis is done uner acidic conditions, for example with perchloric acid or acetic acid. Tetrahydrofuran is a suitable diluent for this reaction mixture. Reaction temperatures of from 10° C. to 100° C. may be employed. The length of time required for hydrolysis is determined in part by the hydrolysis temperature. With acetic acid-water-tetrahydrofuran at about 60° C., several hours are sufficient.

Finally, in step "l" of Chart B, the formula-XX lactol is oxidized to the formula-XXI lactone. Oxidation reagents useful for this transformation are known in the art. An especially useful reagent for this purpose is the Collins reagent, i.e. chromium trioxide in pyridine. See J. C. Collins et al., Tetrahedron Lett., 3363 (1968). Dichloromethane is a suitable diluent for this purpose. A slight excess of the oxidant beyond the amount necessary to oxidize the secondary hydroxy group of the formula-XX intermediate is used. Reaction temperatures of below 20° C. are used. Preferred reaction temperatures are in the range −10° to +10° C. The oxidation proceeds rapidly and is usually complete in about 5 to 20 minutes.

It should be apparent that the formula-XXI lactone of Chart B corresponds to the formula-IX lactone alkene of Chart A wherein "n" is 2, and reference is now made to Chart A for the remaining steps in the process.

Continuing with Chart A, in step "b" the formula-IX alkene is hydroxylated to a glycol of formula X, using general procedures known in the art. See, for example, U.S. Pat. No. 3,781,306. Thus, osmium tetroxide is used, preferably with N-methylmorpholine oxide. Various formula-X glycol isomers are obtained, which can be separated by silica gel chromatography. However, such separation is usually not necessary, since each isomer is useful as an intermediate according to this invention as shown in Chart A.

In step "c" a formula-X glycol or mixture of glycols is transformed to a diester of formula X by stepwise reaction. First the glycol is reacted with an ortho ester of the formula:

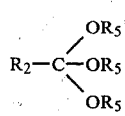

wherein $R_2$ and $R_5$ are as defined above. The reaction goes smoothly in a temperature range of −50° C. to +100° C., although for convenience 0° C. to +50° C. is generally preferred. From 1.5 to 10 molar equivalents of the ortho ester are employed, together with an acid catalyst. The amount of the catalyst is usually a small fraction of the weight of the glycol, say 1%, and a typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
triethyl orthoacetate,
triethyl orthopropionate,
trimethyl orthobutyrate,
triethyl orthovalerate,
trimethyl orthooctanoate,
trimethyl orthophenylacetate, and
trimethyl ortho (2,4-dichlorophenyl)acetate.
Preferred are those ortho esters wherein $R_2$ is alkyl of one to 7 cabon atoms; especially preferred are those wherein $R_2$ is alkyl of one to 4, particularly ethyl.

Continuing with step "c", the reaction product from the ortho ester, a cyclic ortho ester of the formula:

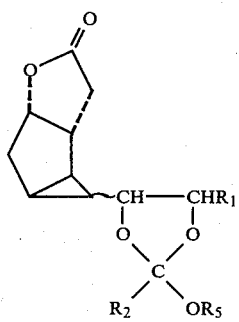

XVII wherein $R_1$, $R_2$, $R_5$, and $\sim$ are as defined above, is converted to the formula-XI diester by reaction of the formula-XVII cyclic ortho ester with anhydrous formic acid. By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°–30° C. and is usually completed within about 10 minutes. Thereafter the formula-XI product is recovered and purified if desired by methods known in the art.

In step "d" the formula-XI product of step "c" is subjected to solvolysis in methanol or ethanol in the presence of a base to remove formyl groups. Examples of the base are sodium or potassium bicarbonate, sodium or potassium carbonate or sodium or potassium alkoxides including methoxides or ethoxides. The reaction is conveniently run in an excess of the solvolysis reagent, for example methanol or ethanol. The temperature range is from −50° C. to 100° C. The time for completion of the reaction varies with the base, requiring several hours with sodium bicarbonate.

In step "e" the free hydroxyl groups of the formula-XV product of step "d" are blocked with blocking groups $R_3$, as defined above. These blocking groups are selected so that they will survive the step "f" hydrolysis of the acyl groups

in alkaline solution but are easily removable under acid conditions.

When the blocking group is tetrahydropyranyl or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess, preferably 1.0 to 1.2 times theory, and the reaction is carried out at about 20°–50° C.

When the blocking group is of the formula

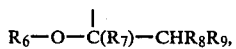

as defined above, the appropriate reagent is a vinyl ether, e.g. ethyl vinyl ether, isopropenyl methyl ether, isobutyl vinyl ether, or any vinyl ether of the formula $R_6-O-C(R_7)=CR_8R_9$ wherein $R_6$, $R_7$, $R_8$, and $R_9$ are as defined above; or an unsaturated cyclic or heterocyclic compound, e.g. 1-cyclohex-1-yl methyl ether

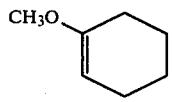

or 5,6-dihydro-4-methoxy-2H-pyran

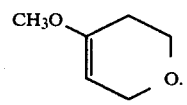

See C. B. Reese et al., J. Am. Chem. Soc. 89, 3366 (1967). The reaction conditions for such vinyl ethers and unsaturates are similar to those for dihydropyran above.

In step "f" the acyl groups of the formula-XII compound are removed by solvolysis in the presence of a base, generally using stronger reagents or more prolonged treatment than for the removal of formyl groups in step "d". Thus, instead of sodium bicarbonate as in step "d", sodium methoxide is useful.

In step "g" the free hydroxyl groups in the side chain of the formula-XIII compound are oxidized to keto groups, using general procedures known in the art. See for example, using general procedures known in the art. See for example, K. E. Pfitzer et al., J. Am. Chem. Soc. 87, 5661 (1965); Fieser and Fieser, Reagents for Organic Synthesis, Vol. 1, John Wiley and Sons, Inc., N.Y., 1967, pages 217 and 637; and J. C. Collins et al., Tetrahedron Lett. 3363 (1968).

When $R_4$ in the formula-VII products is hydrogen, the blocking groups of the formula-XIV product of step "g" are replaced with hydrogen by acid hydrolysis, as shown in step "h", thereby forming product XVI. General procedures are known in the art. For the tetrahydropyranyl groups, for example, the formula-XIV compound is contacted with methanol-HCl or with acetic acid-water-tetrahydrofuran at 40°-55° C.

When $R_4$ in the formula-VII products is carboxyacyl, $R_{10}$, the formula-XVI product of step "h" is carboxylated by methods generally known in the art.

By "carboxyacyl" is meant a group $R_{10}$ which is

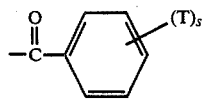 (a)

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms;

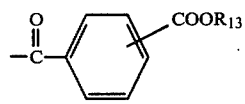 (b)

wherein $R_{13}$ is alkyl of one to 4 carbon atoms, inclusive;

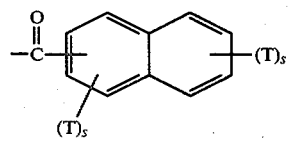

wherein T and s are as defined above; or
(d) lower alkanoyl of 2 to 8 carbon atoms, i.e.

wherein $R_{14}$ is alkyl of one to 7 carbon atoms, inclusive. Examples of alkyl of one to 7 carbon atoms, inclusive, are methyl, ethyl, propyl, butyl, pentyl, hexyl, heptyl, and their isomeric forms.

When $R_{10}$ is an aromatic carboxyacyl group, e.g. a benzoyl, phthaloyl, or naphthoyl type represented by (a), (b), or (c), the carboxylation is accomplished by methods known in the art. Thus an aromatic acid of the formula $R_{10}OH$, wherein $R_{10}$ is as defined above, for example benzoic acid, is reacted with the formula-XVI compound in the presence of a dehydrating agent, e.g. an alkyl or aryl sulfonyl chloride; or an anhydride of the aromatic acid of the formula $(R_{10})_2O$, for example benzoic anhydride, is used.

Preferably, however, an acyl halide, e.g. $R_{10}Cl$, for example benzoyl chloride, is reacted with the formula-XVI compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°-60° C., contacting the reactants in a liquid medium, e.g. excess pyridine or an inert solvent such as benzene, toluene or chloroform. The acylating agent is used either in stoichiometric amount or in excess.

As examples of $R_{10}$ for the purposes of this invention, the following are available as acids ($R_{10}OH$), anhydrides (($R_{10})_2O$), or acyl chlorides ($R_{10}Cl$): benzoyl; substituted benzoyl, e.g. (2-, 3- or 4-)methylbenzoyl, (2-, 3-, or 4-)-ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, 2-, 3-, or 4-phenethylbenzoyl, 2-, 3-, or 4-nitrobenzoyl, (2,4-, 2,5-, or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; monoesterified phthaloyl, e.g.

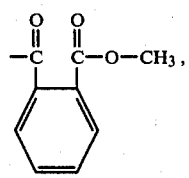

isophthaloyl, e.g.

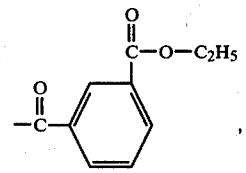

or terephthaloyl, e.g.

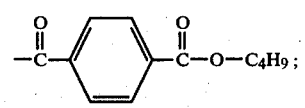

(1- or 2-)naphthoyl; and substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5- or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl. There may be employed, therefore, benzoyl chloride, 4-nitrobenzoyl chloride, 3,5-dinitrobenzoyl chloride, and the like, i.e. $R_{10}Cl$ compounds corresponding to the above $R_{10}$ groups. If the acyl chloride is not available, it is made from the corresponding acid and pgosphorus pentachloride as is known in the art. It is preferred that the $R_{10}OH$, $(R_{10})_2O$, or $R_{10}Cl$ reactant does not have bulky, hindering substituents, e.g. tertbutyl, on both of the ring carbon atoms adjacent to the carbonyl attaching-site.

When $R_{10}$ is lower alkanoyl, the carboxyacylating agent is preferably the anhydride of a lower alkanoic acid, i.e.

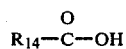

wherein $R_{14}$ is alkyl of one to 7 carbon atoms, inclusive. Examples of such anhydrides are acetic anhydride, propionic anhydride, isobutyric anhydride, and hexanoic acid anhydride.

The carboxyacylation is advantageously carried out by mixing the formula-XVI hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

When $R_4$ in the formula-VII products of this invention is a silyl group $-Si(A)_3$, the formula-XVI compound is transformed to a silyl derivative of formula VII by procedures known in the art. See, for example, Pierce, "Silylation of Organic Compounds," Pierce Chemical Co., Rockford, Ill. (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include
chlorotrimethylsilane,
chloro(t-butyl)dimethylsilane,
chlorotriisobutylsilane,
chlorotriphenylsilane,
chlorotris(p-chlorophenyl)silane,
chlorotri-m-tolylsilane,
and tribenzylchlorosilane.
Alternately, a chlorosilane is used with a corresponding disilazane. Examples of other silylating agents suitable for forming the formula-VII compounds include
pentamethylsilylamine,
pentaethylsilylamine,
N-trimethylsilyldiethylamine,
1,1,1-triethyl-N,N-dimethylsilylamine,
N,N-diisopropyl-1,1,1-trimethylsilylamine,
1,1,1-tributyl-N,N-dimethylsilylamine,
N,N-dibutyl-1,1,1-trimethylsilylamine,
1-isobutyl-N,N,-b 1,1-tetramethylsilylamine,
N-benzyl-N-ethyl-1,1,1-trimthylsilylamine,
N,N,1,1-tetramethyl-1-phenylsilylamine,
N,N-diethyl-1,1-dimethyl-1-phenylsilylamine,
N,N-diethyl-1-methyl-1,1-diphenylsilylamine,
N,N-dibutyl-1,1,1-triphenylsilylamine, and
1-methyl-N,N,1,1-tetraphenylsilylamine.

See, for example, U.S. Pat. No. 3,822,303.

The formula-VII products of this invention are useful intermediates in the synthesis of prostaglandins and analogs.

For example, the formula-VII compound wherein "n" is one, $R_1$ is hydrogen, and $R_4$ is either a blocking group $R_3$, silyl $-Si(A)_3$, or carboxyacyl $R_{10}$, as defined above, is reactive with a Grignard reagent. Using Grignard reagents prepared by reacting magnesium turnings with 1-bromopentane or 1-bromo-cis-2-pentene there are obtained, after suitable work-up and separation of the 3 R and 3 S epimers, the lactone intermediates which are useful in preparing $PGF_{2\alpha}$ and $PGF_{3\alpha}$ by methods known in the art. See, for example, E. J. Corey et al., J. Am. Chem. Soc. 92, 397 (1970) and 93, 1490 (1971).

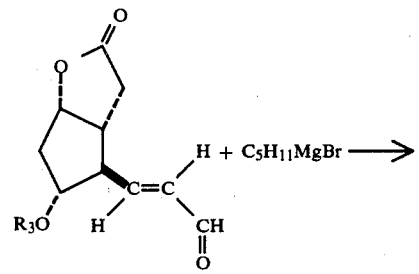

XXII

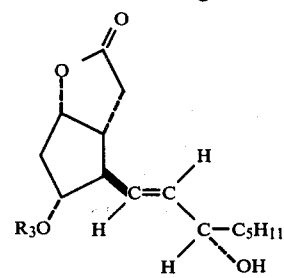

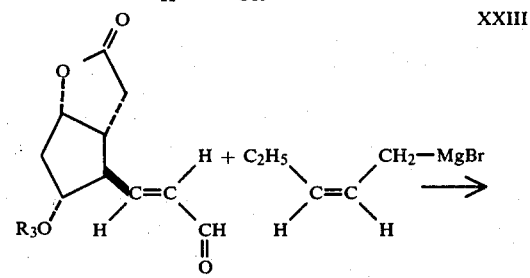

XXIII

Similarly, using the Grignard reagent obtained from 1-bromo-1,1-dimthylpentane, there is obtained the lactone useful in preparing the analog, 16,16-dimethyl-$PGF_{2\alpha}$. See U.S. Pat. No. 3,903,131.

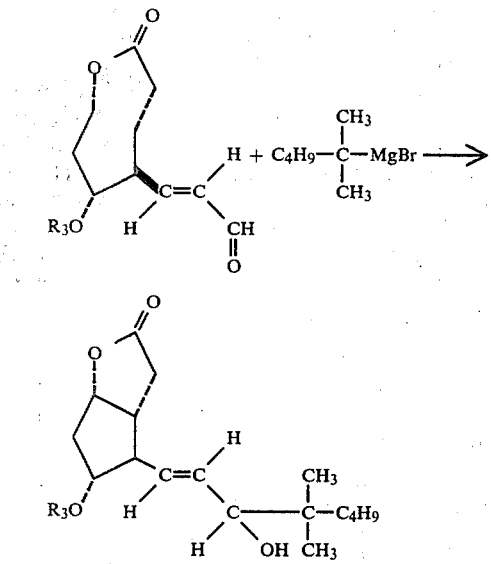

Using the formula-VII compound wherein "n" is one, $R_1$ is methyl and $R_4$ is either a blocking group $R_3$, silyl —$Si(A)_3$, or carboxyacyl $R_{10}$, the Grignard reagent from 1-bromopentane yields the lactone intermediate useful in preparing 15-methyl-$PGF_{2\alpha}$. See, for example, Derwent Farmdoc No. 72340T.

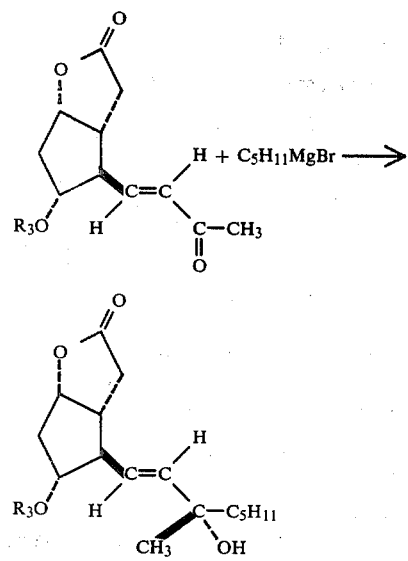

When the formula-VII compound wherein "n" is two, $R_1$ is hydrogen, and $R_4$ is either a blocking group $R_3$ or carboxyacyl $R_{10}$, is reacted with the Grignard reagent from 1-bromopentane there is obtained the lactone suitable for preparing 4,5-didehydro-$PGF_{1\alpha}$. See Derwent Farmdoc No. 69674U.

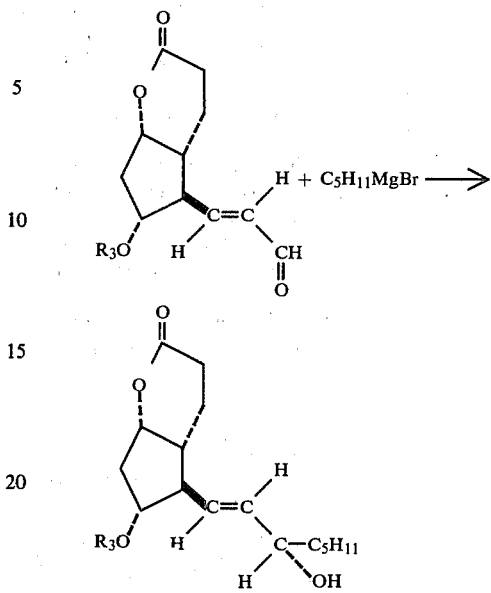

The formula-VII products wherein $R_4$ is an aromatic carboxyacyl group (a), (b), or (c), i.e. a benzoyl, phthaloyl, or naphthoyl type, are especially useful for crystallizing or purifying these acrylic aldehydes.

Those formula-VII products wherein $R_4$ is silyl, —$Si(A)_3$, are useful as intermediates for preparing known useful compounds. For example, following the reaction shown above for compound XXV but replacing $R_3$ with silyl, —$Si(A)_3$, there are obtained compounds of the formula

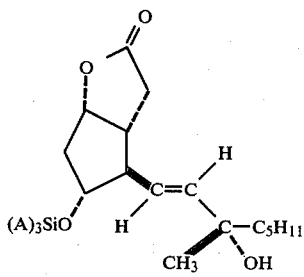

These formula-XXVII compounds are useful for preparing 11-silyl ethers of 15-methyl-$PGF_{2\alpha}$ and thence 15-methyl-$PGE_2$. See for example U.S. Pat. No. 3,822,303. Particularly useful are those formula-VII compounds wherein $R_4$ is t-butyldimethylsilyl.

Subsequent to this invention there has appeared a reference to some of the formula-VII compounds. See Derwent Farmdoc No. 28224W (Ono Pharmaceutical Co.).

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60 spectrophotometer in deuterochloroform solutions with tetramethylsilane as an internal standard (downfield).

"Brine", herein, refers to an aqueous saturated sodium chloride solution.

"Skellysolve B", herein, refers to mixed isomeric hexanes.

"TLC", herein, refers to thin layer chromatography.

Silica gel chromatography, as used herein, is understood to include elution, collection of fractions, and combination of those fractions shown by TLC to contain the desired product free of starting material and impurities.

"Concentrating", as used herein, refers to concentration under reduced pressure, preferably at less than 50 mm. and at temperatures below 35° C.

EXAMPLE 1

Exo-3-hydroxy-endo-6-vinyl-bicyclo[3.1.0]hexan-exo-2-acetic Acid, γ-Lactone (Formula IX: n is one, $R_1$ is hydrogen and ∼ is endo).

Refer to Chart A, step "a". A solution of the formula-VIII tricyclic lactone aldehyde (20 g.) in 150 ml. of benzene is treated at 5°–10° C. with a solution of the ylid prepared from methyltriphenylphosphonium bromide (54 g.) and 95 ml. of 1.6 M butyllithium in one liter of benzene (previously heated at reflux for one hr. and cooled). The addition is completed within 1–1.5 hr., and, after an additional 0.5 hr. stirring, the mixture is filtered and concentrated. The residue is taken up in 100–200 ml. of ethyl acetate-Skellysolve B (40:60) and left standing to crystallize out the by-product triphenylphosphine oxide. After filtration, the filtrate is subjected to silica gel chromatography, eluting with ethyl acetate-Skellysolve B (40:60). There is obtained the formula-IX title compound, 16.2 g., an oil, having NMR peaks at 1.3–3.0, 4.6–4.9, and 5.0–5.4 δ; and $R_f$ 0.74 (TLC on silica gel in ethyl acetate-Skellysolve B (50:50)).

EXAMPLE 2

Endo-6-(1,2-dihydroxyethyl)-exo-3-hydroxybicyclo[3.1.0]hexan-exo-2-acetic Acid, γ-Lactone (Formula-X: n is one, $R_1$ is hydrogen and ∼ is endo).

Refer to Chart A, step "b". A solution of the formula-IX alkene (Example 1, 8.0 g.) in 80 ml. of acetone is treated with a solution of N-methylmorpholine oxide dihydrate (9.0 g.) in 12 ml. of water, followed by a solution of osmium tetroxide (130 mg.) in 6.5 ml. of t-butanol. When the reaction is completed, the acetone is removed under reduced pressure. The residue is diluted with 100 ml. of water, saturated with ammonium sulfate, and extracted with tetrahydrofuran. The organic phase is dried over magnesium sulfate and concentrated under reduced pressure to yield 12 g. of crude oily product. The oil is subjected to silica gel chromatography to yield the formula-X title compound, 8.5 g., an oil, having NMR peaks at 0.7–1.2, 1.3–1.9, 2.4–3.4, 3.4–3.7, 3.7–4.2, and 4.7–5.0 δ; and $R_f$ 0.66 (TLC on silica gel in methanol-dichloromethane (15:85)).

EXAMPLE 3

3α-Formyloxy-5α-hydroxy-2β-(3-propionyloxy-trans-1-propenyl)-1α-cyclopentaneacetic Acid, γ-Lactone (Formula XI: n is one, $R_1$ is hydrogen, and $R_2$ is ethyl).

Refer to Chart A, step "c". A solution of the formula-X glycol (Example 2, 7.2 g.) and triethylorthopropionate (15 g.) in 30 ml. of tetrahydrofuran is treated with 3 μl of trifluoroacetic acid. After one hr. the solvent is removed under reduced pressure and the residue treated with 100 ml. of anhydrous formic acid with stirring. After 15 min. there is added 100 ml. of 1 N. sodium hydroxide and 100 ml. of crushed ice. The mixture is extracted with dichloromethane and the organic phase is washed with 5% aqueous sodium bicarbonate, dried over magnesium sulfate, and concentrated. The oil (9.6 g.) thus obtained is subjected to silica gel chromatography, eluting with ethyl acetate-cyclohexane (1:1), to yield the formula-XI title compound, 4.1 g., having NMR peaks at 1.1, 1.9–3.0, 4.4–4.6, 4.8–5.2, 5.6–5.8, and 8.0 δ; and $R_f$ 0.49 (TLC on silica gel in ethyl acetate-cyclohexane (1:1)).

EXAMPLE 4

3α,5α-Dihydroxy-2β-(3-propionyloxy-trans-1-propenyl)-1α-cyclopentaneacetic Acid, γ-Lactone (Formula XV: n is one, $R_1$ is hydrogen, and $R_2$ is ethyl).

Refer to Chart A, step "d". A solution of the formula-XI formate (Example 3, 4.1 g.) in 35 ml. of dry methanol is treated with sodium bicarbonate (0.5 g.). When the reaction is finished in about 2–3 hr., the solvent is removed under reduced pressure. The residue is partitioned between water and dichloromethane, and the organic phase is dried over magnesium sulfate and concentrated. The oily residue is subjected to silica gel chromatography, eluting with ethyl acetate to yield the formula-XV title compound, 2.8 g., having NMR peaks at 1.13, 3.7–4.3, 4.3–4.7, 4.7–5.2, and 5.5–5.8 δ; and $R_f$ 0.65 (TLC on silica gel in ethyl acetate).

EXAMPLE 5

3α-(1-Ethoxyethoxy)-5α-hydroxy-2β-(3-propionyloxy-trans-1-propenyl)-1α-cyclopentaneacetic Acid, γ-Lactone (Formula-XII: n is one, $R_1$ is hydrogen, $R_2$ is ethyl, and $R_3$ is 1-ethoxyethyl).

Refer to Chart A, step "e". A solution of the formula-XV 5-hydroxy lactone (Example 4, 2.8 g.) in 10 ml. of dichloromethane is treated with 5 ml. of ethyl vinyl ether and 5 mg. of p-toluenesulfonic acid dissolved in 1 ml. of tetrahydrofuran. After the reaction is finished, in about 0.5 hr., the mixture is washed with 5% aqueous sodium bicarbonate. The organic phase is dried over sodium sulfate and concentrated. The residue is subjected to silica gel chromatography, eluting with ethyl acetate-Skellysolve B (60:40) to yield the formula-XII title compound, 3.0 g., having NMR peaks at 1.15, 1.20, 1.27, 4.3–4.5, 4.73, 4.7–5.1, and 5.5–5.8δ; and $R_f$ 0.50 (TLC on silica gel in ethyl acetate-Skellysolve B (1:1)).

EXAMPLE 6

3α-(1-Ethoxyethoxy)-5α-hydroxy-2β-(3-hydroxy-trans-1-propenyl)-1α-cyclopentaneacetic Acid, γ-Lactone (Formula-XIII: n is one, $R_1$ is hydrogen, and $R_3$ is 1-ethoxyethyl).

Refer to Chart A, step "f". The formula-XII propionate, (Example 5, 3.0 g.) in 10 ml. of methanol is added to a solution of sodium methoxide (freshly prepared from 20 mg. of sodium in 40 ml. of anhydrous methanol). After the reaction is complete, in about 20 min., the methanol is removed under reduced pressure. The residue is partitioned between dichloromethane and 0.4 M phosphate buffer of pH 4.5. The organic phase is dried over sodium sulfate and concentrated to yield the formula-XIII title compound, 1.8 g., having $R_f$ 0.18 (TLC on silica gel in ethyl acetate-Skellysolve B (1:1)).

EXAMPLE 7

3α-(1-Ethoxyethoxy)-5α-hydroxy-2β-(trans-2-formylethenyl)-1α-cyclopentaneacetic Acid, γ-Lactone (Formula-XIV: n is one, $R_1$ is hydrogen, and $R_3$ is 1-ethoxyethyl).

Refer to Chart A, step "g". An oxidizing reagent is prepared from chromium trioxide (5.4 g.) and 3,5-dimethylpyrazole (5.2 g.) in 150 ml. of dichloromethane, stirred for 15 min. To the solution is then added the formula-XIII 3-hydroxy compound (Example 6, 1.8 g.) dissolved in 20 ml. of dichloromethane. After the reaction is finished, in about 5 min., the mixture is washed with 5% aqueous bicarbonate. The organic phase is dried over sodium sulfate and concentrated. The residue is subjected to silica gel chromatography, eluting with acetone-dichloromethane (1:9) to yield the formula-XIV title compound, 0.99 g., an oil, having NMR peaks at 1.17, 1.27, 1.7–3.1, 3.1–3.8, 3.8–4.4, 4.75, 4.7–5.2, 5.8–7.0, and 9.55 δ; and $R_f$ 0.70 (TLC on silica gel in acetone-dichloromethane (15:85)).

EXAMPLE 8

3α,5α-Dihydroxy-2β-(trans-2-formylethenyl)-1α-cyclopentaneacetic Acid, γ-Lactone (Formula-XVI: n is one and $R_1$ is hydrogen).

Refer to Chart A, step "h". The formula-XIV ethoxyethyl ester (Example 7, 0.9 g.) is stirred in 4 ml. of isopropyl alcohol and 1 ml. of 0.1 N hydrochloric acid for 24 hr. at about 25° C. The mixture is washed with aqueous 5% sodium bicarbonate and the organic phase is concentrated. The residue is taken up in ethyl acetate, washed with brine, and dried over magnesium sulfate. After concentrating, the residue is subjected to silica gel chromatography eluting with ethyl acetate-hexane (1:1) to yield the formula-XVI title compound in 70% yield. The product has NMR peaks at 3.85–4.48, 4.83–5.24, 6.16, 6.82, 9.41, and 9.55 δ; and infrared spectral peaks at 3450, 2750, 1775, 1680, 1640, and 975 cm$^{-1}$.

EXAMPLE 9

5α-Hydroxy-3α-trimethylsilyloxy-2β-(trans-2-formylethenyl)-1α-cyclopentaneacetic Acid, γ-Lactone (Formula VII: n is one, $R_1$ is hydrogen, and $R_4$ is trimethylsilyl).

The formula-XVI 3-hydroxy compound (Example 8, 0.196 g.) is added to 0.2 ml. of a mixture of trimethylchlorosilanehexamethyldisiloxane-pyridine (3:6:10) and stirred at about 25° C. for 5 min. The mixture was concentrated under reduced pressure, then diluted with benzene, filtered through diatomaceous earth, and concentrated to yield the formula-VII title compound, 0.260 g.) having NMR peaks at 3.82–4.32, 4.68–5.08, 6.02, 6.64, 9.33, and 9.47δ; and infrared spectral peaks at 2750, 1780, 1680, 1640, 970, 840, and 750 cm$^{-1}$.

There is likewise prepared the corresponding formula-VII compound wherein $R_4$ is t-butyldimethyl, starting with the formula-XVI 3-hydroxy compound of Example 8 and following the general procedure of E. J. Corey et al., J. Am. Chem. Soc. 94, 6190 (1972) using dimethyl-tert-butylsilyl chloride in dimethylformamide in the presence of imidazole.

EXAMPLE 10

3α-Benzoyloxy-5-hydroxy-2β-(trans-2-formylethenyl)-1α-cyclopentaneacetic Acid, γ-Lactone (Formula VII: n is one, $R_1$ is hydrogen, and $R_4$ is benzoyl).

Refer to U.S. Pat. No. 3,901,923. The formula-XVI 3-hydroxy compound (Example 8) in dry pyridine is treated with benzoyl chloride at about 20°–40° C. After separation and purification by silica gel chromatography the formula-VII title compound is obtained.

EXAMPLE 11

5α-Hydroxy-3α-(tetrahydro-2H-pyran-2-yloxy)-2β-(trans-2-formylethenyl)-1α-cyclopentaneacetic Acid, γ-Lactone (Formula XIV: n is one, $R_1$ is hydrogen, and $R_4$ is tetrahydropyranyl).

Refer to Chart A. Following the procedures of Examples 5–7 but replacing ethyl vinyl ether with dihydropyran, the formula-XIV title compound is obtained, having NMR peaks at 1.37–1.9, 2.12–3.28, 3.37–4.38, 4.63–4.78, 4.97–5.20, 6.03–7.04, and 9.55 δ; and $R_f$ 0.70 (TLC on silica gel in acetone-dichloromethane (15:85)).

EXAMPLE 12

5α-Hydroxy-3α-(tetrahydro-2H-pyran-2-yloxy)-2β-(3α-hydroxy-4,4-dimethyl-trans-1-octenyl)-1α-cyclopentaneacetic Acid, γ-Lactone (Formula XXIV: $R_3$ is tetrahydropyranyl).

The formula-VII lactone aldehyde (0.40 g.) wherein n is one, $R_1$ is hydrogen, and $R_4$ is tetrahydropyranyl (Example 11, 400 mg.) is added to a Grignard reagent prepared in diethyl ether from 1-chloro-1,1-dimethylpentane and previously cooled to −50° C. After stirring about 0.5 hr. at −50° C., the reaction is quenched with water and ammonium chloride. Dichloromethane is added together with sufficient 1 N hydrochloric acid to dissolve solids. The organic phase is dried over sodium sulfate and concentrated to an oil, 0.665 g., consisting of the title compound and its 3β-hydroxy epimer. The tetrahydropyranyl groups are removed by acid hydrolysis. The alpha and beta epimers are separated by silica gel chromatography and the alpha compound is thereafter converted to 16,16-dimethyl-PGF$_{2\alpha}$.

EXAMPLE 13

5α-Hydroxy-3α-(tetrahydro-2H-pyran-2-yloxy)-2β-(3α-hydroxy-trans-1-octenyl)-1α-cyclopentaneacetic Acid, γ-Lactone (Formula XXII: $R_3$ is tetrahydropyranyl).

Following the procedures of Example 12 but replacing the Grignard reagent with n-pentyl magnesium bromide, the title compound is prepared. It is thereafter converted to PGF$_{2\alpha}$.

EXAMPLE 14

5α-Hydroxy-3α-(tetrahydro-2H-pyran-2-yloxy)-2β-(3α-hydroxy-trans-1-cis-5-octenyl)-1α-cyclopentaneacetic Acid, γ-Lactone (Formula-XXIII: $R_3$ is tetrahydropyranyl).

Following the procedures of Example 12 but replacing the Grignard reagent with that derived from 1-bromo-cis-2-pentene, the title compound is prepared. It is thereafter converted to PGF$_{3\alpha}$.

EXAMPLE 15

3α-(1-Ethoxyethoxy)-5α-hydroxy-2β-(3-oxo-trans-1-butenyl)-1α-cyclopentaneacetic Acid, γ-Lactone (Formula XIV: n is one, $R_1$ is methyl, and $R_3$ is 1-ethoxyethyl).

Refer to Chart A, steps "a" through "g". Following the procedures of Examples 1–7, above, but replacing the ylid in step "a" (Example 1) with the ylid prepared from ethyltriphenylphosphonium bromide, there are obtained the respective compounds of formula IX, X, XI, XV, XII, XIII, and XIV in which $R_1$ is methyl. The formula-XIV title compound is thus obtained.

Following the procedure of Example 13 but replacing the formula-VII lactone aldehyde of that Example with the above formula-XIV ketone, and reacting it with n-pentyl magnesium bromide, there is obtained the corresponding formula-XXV lactone: 3α-(1-ethoxyethoxy)-5α-hydroxy-2β-(3α-hydroxy-3β-methyl-trans-1-octenyl)-1α-cyclopentaneacetic acid, γ-lactone. That lactone is thereafter converted to 15-methyl-PGF$_{2α}$.

EXAMPLE 16

Exo-3-hydroxy-endo-6-vinyl bicyclo[3.1.0]hexan-exo-2-propionic Acid, δ-Lactone (Formula XXI: $R_1$ is hydrogen and ~ is endo).

I. Refer to Chart B, step "i". There is first prepared the formula-XVIII lactol. A solution of the formula-IX lactone (Example 1, 2.7 g.) in 30 ml. of toluene at about −70° C. is treated with 3.6 ml. of diisobutylaluminum hydride in 30 ml. of toluene. After about 0.5 hr. a solution of 12 ml. of tetrahydrofuran and 6 ml. of water is cautiously added. The mixture is filtered and the filtrate is washed with brine, dried, and concentrated to the mixed alpha and beta hydroxy isomers of the formula-XVIII lactol.

II. Referring to step "j", the above formula-XVIII lactol is reacted with methoxymethyltriphenylphosphonium chloride in tetrahydrofuran in the presence of butyllithium. After concentrating the reaction mixture, the organic phase is partitioned between dichloromethane and water, dried, and subjected to silica gel chromatography to yield the formula-XIX enol ether wherein $R_1$ is hydrogen, $R_{12}$ is methyl, and ~ is endo.

III. In step "k", the above formula-XIX enol ether is hydrolyzed in 66% acetic acid at about 55°–60° C. for several hours. Thereafter the reaction mixture is concentrated and subjected to silica gel chromatography to yield the formula-XX δ-lactol.

IV. In step "l", the above formula-XX δ-lactol is oxidized to the lactone in dichloromethane using Collins reagent at about 10° C. The formula-XXI δ-lactone title compound is thus obtained.

The above formula-XXI lactone wherein $R_1$ is hydrogen is thereafter converted to 4,5-didehydro-PGF$_{1α}$.

Following the procedures of Example 16 but starting with the formula-IX compound of Example 15 wherein $R_1$ is methyl, there are obtained the respective compounds of formula XVIII, XIX, XX, and XXI in which $R_1$ is methyl.

The formula-XXI lactone wherein $R_1$ is methyl is thereafter converted to 4,5-didehydro-15-methyl-PGF$_{1α}$.

It is claimed:

1. A compound of the formula

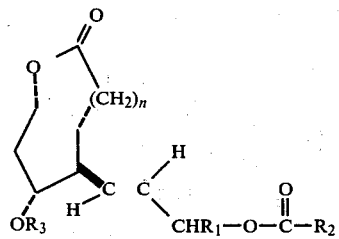

wherein n is one or 2; $R_1$ is hydrogen, methyl, or ethyl; $R_2$ is alkyl of one to 19 carbon atoms, inclusive, or aralkyl of 7 to 12 carbon atoms, inclusive, substituted with zero to 3 halo atoms; and $R_3$ is a blocking group which is tetrahydropyranyl, tetrahydrofuranyl, or a group of the formula

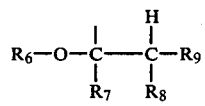

wherein $R_6$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_7$ and $R_8$ are the same or different, being hydrogen, alkyl of one to 4 carbon atoms, inclusive, phenyl or phenyl substituted with one, 2, or 3 alkyl of one to 4 carbon atoms, inclusive, or, when $R_7$ and $R_8$ are taken together, —(CH$_2$)a— or —(CH$_2$)b—O—(CH$_2$)c— wherein a is 3, 4, or 5, b is one, 2, or 3, and c is one, 2, or 3 with the proviso that b plus c is 2, 3, or 4, and wherein $R_9$ is hydrogen or phenyl.

2. A compound according to claim 1 wherein n is one, $R_1$ is hydrogen, $R_2$ is ethyl, and $R_3$ is 1-ethoxyethyl.

* * * * *

UNITED STATES PATENT OFFICE
CERTIFICATE OF CORRECTION

Patent No. 4,235,779     Dated 25 November 1980

Inventor(s) Robert C. Kelly

It is certified that error appears in the above-identified patent and that said Letters Patent are hereby corrected as shown below:

Column 3, line 57, "to T's are" should read -- two T's are --;
Column 5, line 54, the following text should appear:

--
   f) replacing the acyl groups $-\overset{O}{\underset{\|}{C}}-R_2$ in the product of step e) with hydrogen atoms to form a compound of the formula

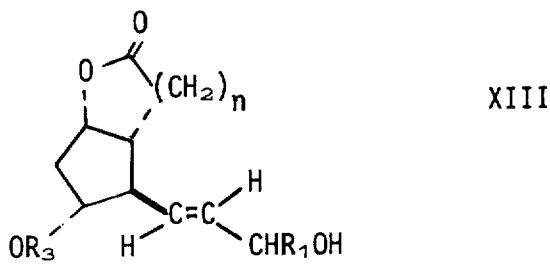

XIII wherein n, $R_1$, and $R_3$ are as defined above;

g) oxidizing the free hydroxyl groups of the product of step f) to form a compound of the formula

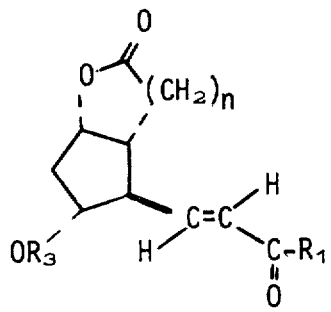

Page 2 of 4 Pages

UNITED STATES PATENT OFFICE
CERTIFICATE OF CORRECTION

Patent No. 4,235,779                    Dated 25 November 1980

Inventor(s)  Robert C. Kelly

It is certified that error appears in the above-identified patent and that said Letters Patent are hereby corrected as shown below:

wherein n, $R_1$, and $R_3$ are as defined above; and h) optionally, when $R_4$ in the product is hydrogen, replacing the blocking group $R_3$ with hydrogen by acid hydrolysis, and, when $R_4$ in the product is silyl or carboxyacyl, further replacing hydrogen at $R_4$ with silyl or carboxyacyl as defined above.

--

Column 6, lines 42-50, that portion of the formula reading

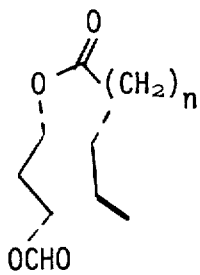     should read     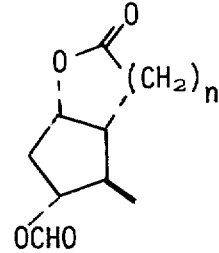

lines 56-66, that portion of the formula reading

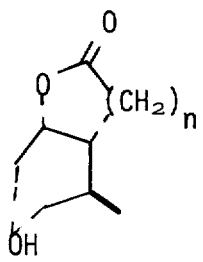     should read     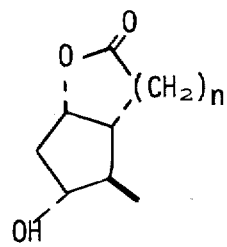

Column 9, line 68, "whereas a low" should read -- whereas at low --;
Column 11, line 20, "7 cabon atoms" should read -- 7 carbon atoms --;

UNITED STATES PATENT OFFICE
CERTIFICATE OF CORRECTION

Patent No. 4,235,779    Dated    25 November 1980

Inventor(s)    Robert C. Kelly

It is certified that error appears in the above-identified patent and that said Letters Patent are hereby corrected as shown below:

Column 14, line 56, "pgosphorus" should read -- phosphorus --;

lines 64-66, "$R_{14}\text{-C-OH}$" should read -- $R_{14}\text{-}\overset{O}{\overset{\|}{C}}\text{-OH}$ --;

Column 15, line 62, "1-isobutyl-N,N-b 1,1-" should read -- 1-isobutyl-$\overset{\sim,\sim//-}{\text{N,N-1,1}}$- --;

Column 17, lines 2-12, that portion of the formula reading

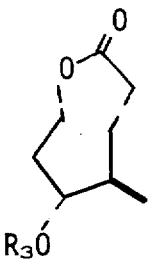         should read         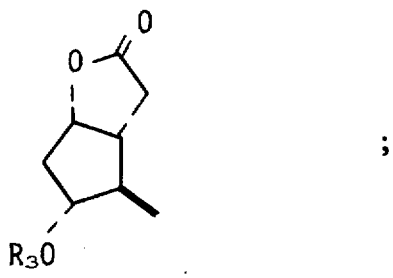    ;

Column 17, lines 15-25,

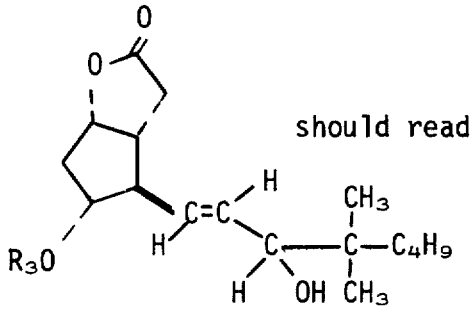         should read         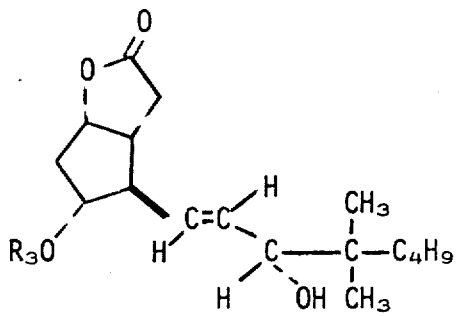

UNITED STATES PATENT OFFICE
CERTIFICATE OF CORRECTION

Patent No. 4,235,779　　　　Dated 25 November 1980

Inventor(s) Robert C. Kelly

It is certified that error appears in the above-identified patent and that said Letters Patent are hereby corrected as shown below:

Column 24, lines 15-25,

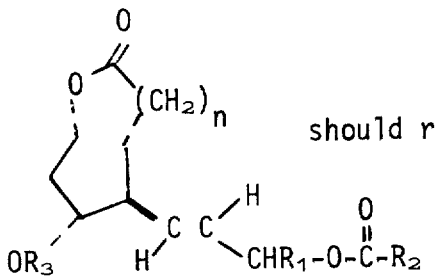 should read 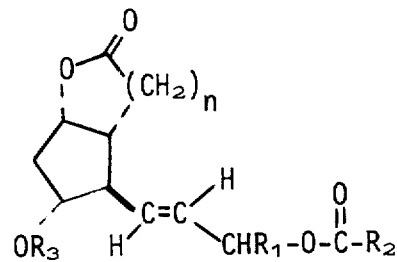

Signed and Sealed this

Nineteenth Day of May 1981

[SEAL]

Attest:

RENE D. TEGTMEYER

*Attesting Officer*　　*Acting Commissioner of Patents and Trademarks*